United States Patent [19]

Bank

[11] Patent Number: 5,126,472
[45] Date of Patent: Jun. 30, 1992

[54] THERMAL DISPROPORTIONATION OF ORGANOOXYSILANES

[75] Inventor: Howard M. Bank, Freeland, Mich.

[73] Assignee: Dow Corning Corporation, Midland, Mich.

[21] Appl. No.: 790,890

[22] Filed: Nov. 12, 1991

[51] Int. Cl.$^5$ .................................................. C07F 7/08
[52] U.S. Cl. .................................................. 556/469
[58] Field of Search ..................................... 556/469

[56] References Cited

U.S. PATENT DOCUMENTS

| | | | |
|---|---|---|---|
| 2,530,367 | 11/1950 | Hance et al. | 556/469 X |
| 2,723,983 | 11/1955 | Bailey | 556/469 |
| 2,746,981 | 5/1956 | Wagner | 556/469 |
| 4,667,047 | 5/1987 | Imaki et al. | 556/469 |

FOREIGN PATENT DOCUMENTS 62-263189 11/1987 Japan .

OTHER PUBLICATIONS

Gilmon et al., J. Org. Chem., 23:326-328 (1958).
Eaborn et al., J. Organometal. Chem., 4:489 (1965).

*Primary Examiner*—Paul F. Shaver
*Attorney, Agent, or Firm*—William F. Boley

[57] ABSTRACT

The present invention is a process for the thermal disproportionation of organooxysilanes containing at least one hydrogen, one organooxy, and one cyclic substitutent all bonded to a single silicon atom, where the cyclic substituent is selected from a group consisting of aryls, substituted aryls, cycloalkyls, and substituted cycloalkyls. The process involves heating the organooxysilanes in a liquid phase to a temperature within a range of about 250° C. to 450° C. The present process is particularly useful for the disproportionation of phenyldialkoxysilanes to diphenydialkoxysilanes and cycloalkyldialkoxysilanes to dicyclodialkoxysilanes.

12 Claims, No Drawings

THERMAL DISPROPORTIONATION OF ORGANOOXYSILANES

BACKGROUND

The present invention is a process for the thermal disproportionation of organooxysilanes containing at least one hydrogen, one organooxy, and one cyclic substituent all bonded to a single silicon atom where the cyclic substituent is selected from a group consisting of aryls, substituted aryls, cycloalkyls, and substituted cycloalkyls. The process comprises heating the organooxysilanes in a liquid phase to a temperature within a range of about 250° C. to 450° C.

It is known that disproportionation of monoaryldichlorosilanes occurs in the presence of Friedel-Crafts type catalysts. For example, Wagner, U.S. Pat. No. 2,746,981, issued May 22, 1956. describes a process for the disproportionation of an aryldichlorosilane containing one aryl group and one hydrogen group by heating the aryldichlorosilane to a temperature of at least 50° C. and a pressure not to exceed atmospheric in the presence of a Friedel-Crafts type catalyst taken from the class consisting of aluminum chloride and boron chloride, and recovering a diarydichlorosilane.

Japanese Patent 62263189, Published Nov. 16, 1987, describes the use of Lewis acid compounds for the disproportionation of aryldihalosilanes under reduced pressure. The catalysts used are described as Lewis acid compounds such as metal halides and aryl metal compounds. Examples of catalysts described in the Japanese patent are aluminum chloride, aluminum bromide, triphenylborane, and tolylborane.

In general, these processes involving the use of a catalyst require that the catalyst either be removed or neutralized prior to distillation to separate desired product. If the catalyst is not removed, the desired product can be disproportionated during the distillation process, reducing process yield. In addition catalysts such as AlCl3 easily sublime coating the processing equipment. Therefore, it is an objective of the present invention to provide a disproportionation process that does not present these problems typically associated with the use of catalysts.

Gilman et al., J. Org. Chem. 23:326-328 (1958), describes the uncatalyzed disproportionation of Ph2SiH2 at 100° C. to 300° C. at atmospheric pressure.

Eaborn et al., J. Organometal. Chem. 4:489 (1965), describes a process where phenyltrimethylsilane and trichlorosilane are reacted at 500° C. in the gas phase to give phenyltrichlorosilane and trimethylsilane.

The cited art does not recognize that organooxysilanes described for use in the present process can be thermally disproportionated. Therefore, it is an objection of the present invention to provide a process for the thermal disproportion of organooxysilanes. Another objective is to provide a process that does not require a catalyst, thus avoiding the previously mentioned problems typically associated with the use of catalysts to disproportionate arylhalosilanes.

SUMMARY OF INVENTION

The present invention is a process for the thermal disproportionation of organooxysilanes containing at least one hydrogen, one organooxy, and one cyclic substituent all bonded to a single silicon atom, where the cyclic substituent is selected from a group consisting of aryls substituted aryls, cycloalkyls, and substituted cycloalkyls. The process involves heating the organooxysilanes in a liquid phase to a temperature within a range of about 250° C. to 450° C.

The present process is particularly useful for the disproportionation of phenyldialkoxysilanes to diphenydialkoxysilanes and cycloalkyldialkoxysilanes to dicyclodialkoxysilanes.

DESCRIPTION OF INVENTION

The present invention is a process for thermal disproportionation of organooxysilanes. The process comprises: heating organooxysilanes of formula $$R_a R^1_b H_c Si(OR^2)_{4-a-b-c}, \quad (1)$$

in liquid phase, at a temperature within a range of about 250° C. to 450° C. for a reaction time within a range of about 0.1 to 18 hours, to effect disproportionation to product organooxysilanes of formula $$R_d R^1_e H_f Si(OR^2)_{4-d-e-f}, \quad (2)$$

where each R is independently selected from a group consisting of aryls, substituted aryls cycloalkyls of three to 20 carbon atoms, and substituted cycloalkyls of three to 20 carbon atoms; $R^1$ is selected from a group consisting of alkyls of one to 20 carbon atoms, each $R^2$ is independently selected from a group consisting of R and $R^1$, a=1 or 2, b=0 or 1, c=1 or 2, a+b+c=2 or 3, d=2 or 3, e=0 or 1, f=0 or 1, and d+e+f=2 or 3.

Organooxysilanes which can be thermally disproportionated by the present process are described by formula (1). The organooxysilanes can contain one or two substituents R. Each R is a radical independently selected from a group consisting of aryls, substituted aryls, cycloalkyls or three to 20 carbon atoms, and substituted cycloalkyls of three to 20 carbons. By "substituted aryl and substituted cycloalkyls" it is meant that one or more of the carbons forming the cyclic ring is substituted with a substituent selected from the group consisting of an alkyl or haloalkyl of one to 20 carbon atoms, chlorine, and bromine. The radical R can be, for example, phenyl, tolyl, xylyl, chlorobenzyl, dichlorobenzyl, cyclopentyl, cyclohexyl methylcyclohexyl, and chlorocyclohexyl. Preferred is when R is selected from the group consisting of phenyl, cyclopentyl, and cyclohexyl.

The organooxysilane described by formula 1 can contain zero or one substituent $R^1$, where each $R^1$ is a radical independently selected from a group consisting of alkyls of one to 20 carbon atoms. $R^1$ can be, for example, methyl, ethyl, propyl, isopropyl, butyl, tert-butyl, and decyl. Preferred is when $R^1$ is methyl.

The organooxysilane described by formula 1 can contain one or two independently selected organooxy radicals of formula —$OR^2$, where each $R^2$ is independently selected from a group consisting of R and $R^1$, as previously described. Preferred is when $R^2$ is selected from a group consisting of methyl, ethyl, and phenyl. Most preferred is when the organooxysilane is substituted with two methoxy radicals.

The organooxysilane described by formula 1 must contain at least one hydrogen bonded to the silicon atom and can contain a maximum of two hydrogen atoms bonded to the silicon atom. It is preferred that the organooxysilane contain one hydrogen atom bonded to the silicon atom.

Examples of organooxysilanes useful in the present process include: phenyldimethoxysilane phenyldiethoxysilane, phenylphenoxysilane, methylphenylmethoxysilane chlorobenzyldimethoxysilane, cyclopentyldimethoxysilane, cyclopentyldiethoxysilane, cyclohexyldimethoxysilane, (methylcyclohexyl)dimethoxysilane, and dicyclohexylmethoxysilane.

The organooxysilane is heated in the liquid phase at a temperature within a range of about 250° C. to 450° C. A preferred temperature for the process is within a range of about 300° C. to 400° C.

The present process can be run in any standard pressure reactor capable of maintaining sufficient pressure to keep the organooxysilanes in the liquid phase at process temperatures. A preferred reactor designed is a continuous flow high-pressure coil.

The time required for the disproportion of the organooxysilanes to occur depends on the temperature at which the process is conducted. In general reaction times within a range of about 0.1 minute to 18 hours are useful. Preferred is a reaction time within a range of about 0.5 hour to four hours.

Product organooxysilanes, which can be formed by the present process, are represented by formula 2 where R, $R^1$, and $R^2$ are as previously described. In the described process, two organooxysilane molecules disproportionate effecting an exchange of an R substituent of one organooxysilane molecule for a hydrogen on the silicon atom of the other organooxysilane. Those skilled in the art will recognize that as a result of this disproportionation reaction, an organooxysilane molecule containing an additional R substituent and a second organooxysilane containing an additional hydrogen will be formed.

The inventor believes that this disproportionation is an equilibrium reaction, where an equilibrium is formed between the organooxysilane and the product organooxysilane. Therefore, it may be desirable to separate the equilibrium mixture, by a process such as distillation and recycle the recovered organooxysilanes back to the present process.

Examples of product organooxysilanes which can be formed by the present process include: diphenyldimethoxysilane, diphenyldiethoxysilane, triphenylmethoxysilane, methyldiphenylmethoxysilane, di(chlorobenzyl)dimethoxysilane, dicyclopentyldimethoxysilane, dicyclopentyldiethoxysilane dicyclohexyldimethoxysilane, di(methylcyclohexyl)dimethoxysilane, and dicyclohexyldimethoxysilane.

To aid in under standing of the present invention, the following example is provided. The example is provided for illustration only and is not intended to limit the present claims.

Example. The thermal disproportionation of phenyldimethoxysilane (PhHSi(OMe)$_2$) at 350° C. was evaluated. The evaluation was conducted in a sealed, 8 mm by 25 cm, Pyrex Brand tube. Prior to sealing and use, the Pyrex tube was dried at 120° C. for two hours. A 1.0 ml aliquot of phenyldimethoxysilane was added to the dried Pyrex Brand tube and the tube sealed. The tube was then heated in a tube heater, maintained at 350° C. for three hours. At the end of the three hours, the tube was placed in dry ice to cool.

The content of the tube was evaluated using gas liquid chromatography (GLC) with a flame ionization detector (FID) The results are presented in Table 1 as the area percent under the GLC-FID trace, for each of the described compounds.

TABLE 1

| Thermal Disproportionation of PhHSi (OMe)$_2$ at 350° C. | |
|---|---|
| Compound | GLC-FID Area % |
| HSi (OMe)$_3$ | 2.5 |
| Si (OMe)$_4$ | 5.5 |
| PhSiH$_3$ | 5.1 |
| PhH$_2$ SiOMe | 0.8 |
| PhHSi (OMe)$_2$ | 7.3 |
| PhSi (OMe)$_3$ | 32.3 |
| Ph$_2$ SiH$_2$ | 10.3 |
| Ph$_2$ HSiOMe | 5.7 |
| Ph$_2$ Si (OMe)$_2$ | 13.3 |
| Ph$_3$ SiH | 10.3 |

What is claimed is:

1. A process for thermal disproportionation of organooxysilanes, the process comprising: heating organooxysilanes of formula

in liquid phase, at a temperature within a range of about 250° C. to 450° C. for a reaction time within a range of about 0.1 to 18 hours, to effect disproportionation to product organooxysilanes of formula

where each R is independently selected from a group consisting of aryls, substituted aryls, cycloalkyls of three to 20 carbon atoms, and substituted cycloalkyls of three to 20 carbon atoms; $R^1$ is selected from a group consisting of alkyls of one to 20 carbon atoms, each R is independently selected from a group consisting of R and $R^1$, a=1 or 2, b=0 or 1, c=1 or 2, a+b+c=2 or 3, d=2 or 3, e=0 or 1, f=0 or 1, and d+e+f=2 or 3.

2. A process according to claim 1, where R is selected from a group consisting of phenyl, cyclopentyl, and cyclohexyl.

3. A process according to claim 1, where R is phenyl.

4. A process according to claim 1, where $R^1$ is methyl.

5. A process according to claim 1, where $R^2$ is selected from a group consisting of methyl, ethyl, and phenyl.

6. A process according to claim 1, where the organooxysilane is phenyldimethoxysilane.

7. A process according to claim 1, where the temperature is within a range of about 300° C. to 400° C.

8. A process according to claim 1, where the reaction time is within a range of about 0.5 hour to four hours.

9. A process according to claim 1 where the product organooxysilanes are selected from a group consisting of diphenyldimethoxysilane, methyldiphenylmethoxysilane, dicyclopentyldimethoxysilane, and dicyclohexyldimethoxysilane.

10. A process according to claim 1, where the product organooxysilane is diphenyldimethoxysilane.

11. A process according to claim 1, where the process is conducted in a continuous-flow high pressure coil type reactor.

12. A process for thermal disproportionation of phenyldimethoxysilane, the process comprising heating phenyldimethoxysilane in liquid phase at a temperature within a range of about 300° C. to 400° C. for a reaction time within a range of about 0.5 hour to four hours, to effect disproportionation to a mixture comprising diphenyldimethoxysilane and dimethoxysilane.

* * * * *